US012600990B2

(12) United States Patent
Day et al.

(10) Patent No.: US 12,600,990 B2
(45) Date of Patent: Apr. 14, 2026

(54) MRNA INDUCED EXPRESSION OF BONE MORPHOGENIC PROTEIN AND RECEPTOR AND METHODS RELATED THERETO

(71) Applicants: Alexander Day, Cleveland, OH (US); Bradford Mullin, New Albany, OH (US)

(72) Inventors: Alexander Day, Cleveland, OH (US); Bradford Mullin, New Albany, OH (US)

( * ) Notice: Subject to any disclaimer, the term of this patent is extended or adjusted under 35 U.S.C. 154(b) by 417 days.

(21) Appl. No.: 18/246,062

(22) PCT Filed: Oct. 3, 2022

(86) PCT No.: PCT/US2022/077467
§ 371 (c)(1),
(2) Date: Mar. 21, 2023

(87) PCT Pub. No.: WO2023/060041
PCT Pub. Date: Apr. 13, 2023

(65) Prior Publication Data
US 2024/0200101 A1      Jun. 20, 2024

Related U.S. Application Data

(60) Provisional application No. 63/252,373, filed on Oct. 5, 2021.

(51) Int. Cl.
| | |
|---|---|
| *C12N 15/88* | (2006.01) |
| *A61K 47/54* | (2017.01) |
| *A61K 48/00* | (2006.01) |
| *C07K 14/51* | (2006.01) |

(52) U.S. Cl.
CPC ............ *C12N 15/88* (2013.01); *A61K 47/543* (2017.08); *A61K 48/0041* (2013.01); *C07K 14/51* (2013.01)

(58) Field of Classification Search
CPC .. C12N 15/88; A61K 47/543; A61K 48/0041; C07K 14/51
See application file for complete search history.

(56) References Cited

U.S. PATENT DOCUMENTS

| | | | | |
|---|---|---|---|---|
| 2010/0119492 A1* | 5/2010 | Hans | ................... | A61L 27/3895 |
| | | | | 435/283.1 |
| 2018/0214572 A1* | 8/2018 | Balmayor | .............. | A61K 35/28 |

FOREIGN PATENT DOCUMENTS

| | | |
|---|---|---|
| KR | 20110132579 A | 12/2011 |
| WO | 2016118697 A1 | 7/2016 |
| WO | 2021003300 A1 | 1/2021 |

OTHER PUBLICATIONS

R. Gao, et al. "Human Spinal Bone Dust as a Potential Local Autograft," Spine 43 (4), 2018, E193-199. (Year: 2018).*
S. Du Pen. "Implantable Spinal Catheter and Drug Delivery Systems: Complications," Techniques in Regional Anesthesia and Pain Management 2.3 (1998): 152-160. (Year: 1998).*
A. McArdle et al. "Positive selection for bone morphogenetic protein receptor type-IB promotes differentiation and specification of human adipose-derived stromal cells toward an osteogenic lineage," Tissue Engineering: Part A, col. 20, Nos. 21 and 22, 2014, 10 pages (Year: 2014).*
International Search Report and Written Opinion issued Jan. 30, 2023 for PCT/US2022/077467, 8 pages.
Mcardle et al., "Positive selection for bone morphogenetic protein receptor type-IB promotes differentiation and specification of human adipose-derived stromal cells toward an osteogenic lineage," Tissue Engineering: Part A vol. 20, Nos. 21 and 22, 2014, 10 pages.
Carragee et al., "A critical review of recombinant human bone morphogenetic protein-2 trials in spinal surgery: emerging safety concerns and lessons learned," The Spine Journall: Official Journal of the North American Spine Society, 11(6), 471-491, 2011, https://doi.org/10.1016/J.SPINEE.2011.04.023.
Geng et al., "BMP-2 and VEGF-A modRNAs in collagen scaffold synergistically drive bone repair through osteogenic and angiogenic pathways," Communications Biology, 4(1), 2021, https://doi.org/10.1038/S42003-020-01606-9.
Katagiri et al., "Bone Morphogenetic Proteins," Cold Spring Harbor Perspectives in Biology, 8(6), 2016, https://doi.org/10.1101/CSHPERSPECT.A021899.
Tannoury et al., "Complications with the use of bone morphogenetic protein 2 (BMP-2) in spine surgery," The Spine Journal, 14(3), 552-559, 2014, https://doi.org/10.1016/J.SPINEE.2013.08.060.
Anttila et al., "Synthetic mRNA Encoding VEGF-A in Patients Undergoing Coronary Artery Bypass Grafting: Design of a Phase 2a Clinical Trial," Molecular Therapy—Methods & Clinical Development, 18, 464-472, 2020, https://doi.org/10.1016/J.OMTM.2020.05.030.
Balmayor et al., "Chemically modified RNA induces osteogenesis of stem cells and human tissue explants as well as accelerates bone healing in rats," Biomaterials, 87, 131-146, 2016, https://doi.org/10.1016/J.BIOMATERIALS.2016.02.018.
Bragdon et al., "Bone morphogenetic proteins: a critical review," Cellular Signalling, 23(4), 609-620, 2011, https://doi.org/10.1016/J.CELLSIG.2010.10.003.
Collen et al., "VEGFA mRNA for regenerative treatment of heart failure," Nature Reviews Drug Discovery, 2021 21:1, 21(1), 79-80. https://doi.org/10.1038/s41573-021-00355-6.

(Continued)

*Primary Examiner* — Michael P Cohen
(74) *Attorney, Agent, or Firm* — Vorys, Sater, Seymour and Pease LLP; Rex W. Miller, II

(57) ABSTRACT

Methods and treatments including preparing a synthetic messenger ribonucleic acid (mRNA) encoding at least for a bone morphogenic protein (BMP) and/or a BMP receptor. The synthetic mRNA is lipid-solubilized in a lipid or lipid derivative carrier. Intraoperatively, a bone harvest sample is obtained and incubated with the lipid-solubilized mRNA. The bone harvest sample internalizes at least a portion of the lipid-solubilized mRNA, thereby forming activated BMP and/or BMPR material. The activated BMP and/or BMPR material may be delivered intraoperatively to a bone fusion bed.

20 Claims, 2 Drawing Sheets

(56)                    References Cited

OTHER PUBLICATIONS

Elkhalifa et al., "Chemically modified mRNA beyond COVID-19: Potential preventive and therapeutic applications for targeting chronic diseases," Biomedicine & Pharmacotherapy, 145, 112385, 2022, https://doi.org/10.1016/J. BIOPHA.2021.112385.

Epstein, "Pros, cons, and costs of INFUSE in spinal surgery," Surgical Neurology International, 2(1), 2011, https://doi.org/10.4103/2152-7806.76147.

Epstein, "Complications due to the use of BMP/INFUSE in spine surgery: The evidence continues to mount," Surgical Neurology International, 4(Suppl 5), S343, 2013, https://doi.org/10.4103/2152-7806.114813.

Faundez et al., "Bone morphogenetic protein use in spine surgery-complications and outcomes: a systematic review," International Orthopaedics, 40(6), 1309-1319, 2016, https://doi.org/10.1007/S00264-016-3149-8.

Gao et al., "Human Spinal Bone Dust as a Potential Local Autograft In Vitro Potent Anabolic Effect on Human Osteoblasts," 2018, https://doi.org/10.1097/BRS.0000000000002331.

Hou et al., "Lipid nanoparticles for mRNA delivery," Nature Reviews Materials 2021, 1-17. https://doi.org/10.1038/s41578-021-00358-0.

Ichiyanagi et al., "Isolation of mesenchymal stem cells from bone marrow wastes of spinal fusion procedure (TLIF) for low back pain patients and preparation of bone dusts for transplantable autologous bone graft with a serum glue," BioScience Trends, 4(3), 110-118, 2010, www.biosciencetrends.com.

Kariko et al., "Incorporation of Pseudouridine Into mRNA Yields Superior Nonimmunogenic Vector With Increased Translational Capacity and Biological Stability," Molecular Therapy, 16(11), 1833-1840,2008, https://doi.org/10.1038/MT.2008.200.

Khorsand et al., "A Comparative Study of the Bone Regenerative Effect of Chemically Modified RNA Encoding BMP-2 or BMP-9," AAPS Journal, 19(2), 2017, 438-446.

Kormann et al., "Expression of therapeutic proteins after delivery of chemically modified mRNA in mice," Nature Biotechnology 2011 29:2, 29(2), 154-157. https://doi.org/10.1038/nbt.1733.

Mannion et al., "Promoting fusion in minimally invasive lumbar interbody stabilization with low-dose bone morphogenic protein-2—but what is the cost?" The Spine Journall: Official Journal of the North American Spine Society, 11(6), 527-533, 2011, https://doi.org/10.1016/J.SPINEE.2010.07.005.

Nohe et al., "Signal transduction of bone morphogenetic protein receptors," Cellular Signalling, 16(3), 291-299, 2004, https://doi.org/10.1016/j.cellsig.2003.08.011.

Sahin et al., "mRNA-based therapeutics—developing a new class of drugs," Nature Reviews Drug Discovery 2014 13:10, 13(10), 759-780. https://doi.org/10.1038/nrd4278.

Sanchez-Duffhues et al., "Bone morphogenetic protein receptors: Structure, function and targeting by selective small molecule kinase inhibitors," Bone, 138, 115472, 2020, https://doi.org/10.1016/J.BONE.2020.115472.

Boden et al., "Use of recombinant human bone morphogenetic protein-2 to achieve posterolateral lumbar spine fusion in humans: a prospective, randomized clinical pilot trial: 2002 Volvo Award in clinical studies," Spine, 27(23), 2662-2673, 2002, https://doi.org/10.1097/00007632-200212010-00005.

Boden et al., "The use of rhBMP-2 in interbody fusion cages. Definitive evidence of osteoinduction in humans: a preliminary report," Spine, 25(3), 376-381, 2000, https://doi.org/10.1097/00007632-200002010-00020.

Behzadi et al., "Cellular uptake of nanoparticles: journey inside the cell," Chemical Society Reviews, 46(14), 4218-4244, 2017, https://doi.org/10.1039/C6CS00636A.

David et al., "Lumbar spinal fusion using recombinant human bone morphogenetic protein in the canine. A comparison of three dosages and two carriers," Spine, 24(19), 1973-1979, 1999, https://doi.org/10.1097/00007632-199910010-00002.

James et al., "A Review of the Clinical Side Effects of Bone Morphogenetic Protein-2," Tissue Eng Part B Rev., Aug. 22, 2016(4):284-97. doi: 10.1089/ten.TEB.2015.0357.

Wang et al., "Bone Morphogenetic Protein (BMP) signaling in development and human diseases," Genes & Diseases, 1(1), 87-105, 2014, https://doi.org/10.1016/J.GENDIS.2014.07.005.

Yu et al., "Cell-mediated delivery of VEGF modified mRNA enhances blood vessel regeneration and ameliorates murine critical limb ischemia," Journal of Controlled Release, 310, 103-114, 2019, https://doi.org/10.1016/J.JCONREL.2019.08.014.

Zhang et al., "Demineralized Bone Matrix Carriers and their Clinical Applications: An Overview," Orthopaedic Surgery, 11(5), 725, 2019, https://doi.org/10.1111/OS.12509.

Schimandle et al., "Experimental spinal fusion with recombinant human bone morphogenetic protein-2," Spine, 20(12), 1326-1337, 1995, https://europepmc.org/article/med/7676329.

* cited by examiner

MRNA INDUCED EXPRESSION OF BONE MORPHOGENIC PROTEIN AND RECEPTOR AND METHODS RELATED THERETO

CROSS-REFERENCE TO RELATED APPLICATIONS

This application claims priority to U.S. patent application Ser. No. 63/252,373, filed on Oct. 5, 2021, and titled "mRNA Induced Expression of Bone Morphogenic Protein and its Receptor in Perioperatively Harvested Bone Forming Cells."

FIELD

The present disclosure relates to mRNA induced expression of one or more proteins and related protein receptors and methods related thereto. More particularly, the present disclosure relates to endogenous synthetic mRNA induced overexpression of bone morphogenic protein and bone morphogenic protein receptor within autologous bone harvest samples.

BACKGROUND

Bone morphogenic proteins (BMPs) are natural growth factors that are vital to a broad spectrum of biological activities in various tissues and, particularly, are critical signaling molecules in the induction of bone and cartilage forming cells. As such, BMPs represent a valuable therapeutic potential for various orthopedic procedures, including bone formation, bone (e.g., long bone) nonunions, spinal fusions, and any other bone fusions (e.g., facial bone fusion) (collectively "bone fusions," unless otherwise indicated). Bone fusion orthopedic procedures have been of particular interest for BMPS due to the need for a bone graft substitute for current autologous bone grafting methods. Current autologous bone grafting methods utilize local site harvest (i.e., at or near the location of an injury) or donor site harvest (i.e., at a location other than an injury, which is typically iliac (pelvis) crest bone), which is often combined with allogenic bone materials. These current methods have reported nonunion rate of up to 30% and are associated with considerable donor site morbidity, thus presenting serious risks to patients. BMPs offer a promising alternative by eliminating the need for current autologous grafting methods and, thus, potentially decreasing the percentage and rate of nonunion. Indeed, available preclinical studies of the efficacy of BMP in spinal fusions demonstrate that BMPs can be a successful alternative to iliac crest autologous bone grafting with a lower rate of nonunion in animal models, including humans. Moreover, such studies demonstrate that the use of BMPs can result in decreased operative time, decreased blood loss, and decreased hospitalization time compared to iliac crest autologous bone grafting.

In 2002, the United States Food and Drug Administration (FDA) approved the use of BMPs for anterior lumbar interbody fusions using a lumbar fusion device. Thereafter, off-label use increased dramatically, with a reported usage of up to 25% for all spinal fusions, for example, in the United States by 2006. Associated complications followed, including ectopic bone formation, neutralizing antibody development against BMP, graft migration, vertebral osteolysis, and severe inflammation (e.g., seroma formation, radiculitis, spine swelling). In response, in 2008, the FDA advised against the off-label use of BMPs for all cervical spinal fusion treatments and, more generally, the use of BMPs on all bone fusion treatments until further research was conducted. Nevertheless, the use of BMPs for bone fusions, including spinal fusions, remains prevalent.

The current methodology for the use of BMPs in a surgical context involves supraphysiologic concentrations thereof to induce bone formation and spinal fusions, in which recombinant human BMP is attached to a collagen matrix and embedded into the fusion site. Supraphysiologic concentrations in "bursts" are used to achieve therapeutic efficacy in view of the short half-life period associated with BMPs (e.g., BMP2 has a half-life of about 7 to 16 minutes). As the collagen matrix breaks down over time, a consistent high concentration of BMPs are released (e.g., 1.5 mg/ml). However, the current methodology is non-specific, failing to limit BMP action to bone forming cell activity (e.g., non-canonical signaling, leakage to surrounding tissue outside of fusion site). Moreover, various adverse effects have been associated with such high concentration of BMPs that are eluted according to the current methodology, including interference with the functioning of essential organ systems by activating expression of inflammatory cytokines and chemokines, activating osteoclasts (which degrade bone), and activating adipogenesis signaling. Studies have shown that these side effects can be reduced with a reduction in the concentration of BMPs, but at a cost of an increase in nonunions.

Accordingly, a need exists for a targeted approach for the use of BMPs to treat spinal and other bone fusions at low BMP concentration to avoid adverse effects, without compromising rate of nonunion.

SUMMARY

These and other features and attributes of the present disclosure and their advantageous applications and/or uses will be apparent from the detailed description which follows.

In one or more aspects, the present disclosure provides a method including preparing a synthetic messenger ribonucleic acid (mRNA) encoding at least for a bone morphogenic protein (BMP); lipid-solubilizing the synthetic mRNA in a lipid or lipid derivative carrier, thereby forming a lipid-solubilized mRNA; obtaining intraoperatively a bone harvest sample; incubating intraoperatively the lipid-solubilized mRNA and the bone harvest sample, whereby the bone harvest sample internalizes at least a portion of the lipid-solubilized mRNA, thereby forming activated BMP material; and delivering intraoperatively the activated BMP material to a bone fusion bed.

In one or more aspects, the present disclosure provides a method including preparing a synthetic messenger ribonucleic acid (mRNA) encoding at least for a bone morphogenic protein receptor (BMPR); lipid-solubilizing the synthetic mRNA in a lipid or lipid derivative carrier, thereby forming a lipid-solubilized mRNA; obtaining intraoperatively a bone harvest sample; incubating intraoperatively the lipid-solubilized mRNA and the bone harvest sample, whereby the bone harvest sample internalizes at least a portion of the lipid-solubilized mRNA, thereby forming activated BMPR material; and delivering intraoperatively the activated BMPR material to a bone fusion bed.

BRIEF DESCRIPTION OF THE DRAWINGS

To assist those of ordinary skill in the relevant art in making and using the subject matter hereof, reference is made to the appended drawings. The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION

Figure 1:
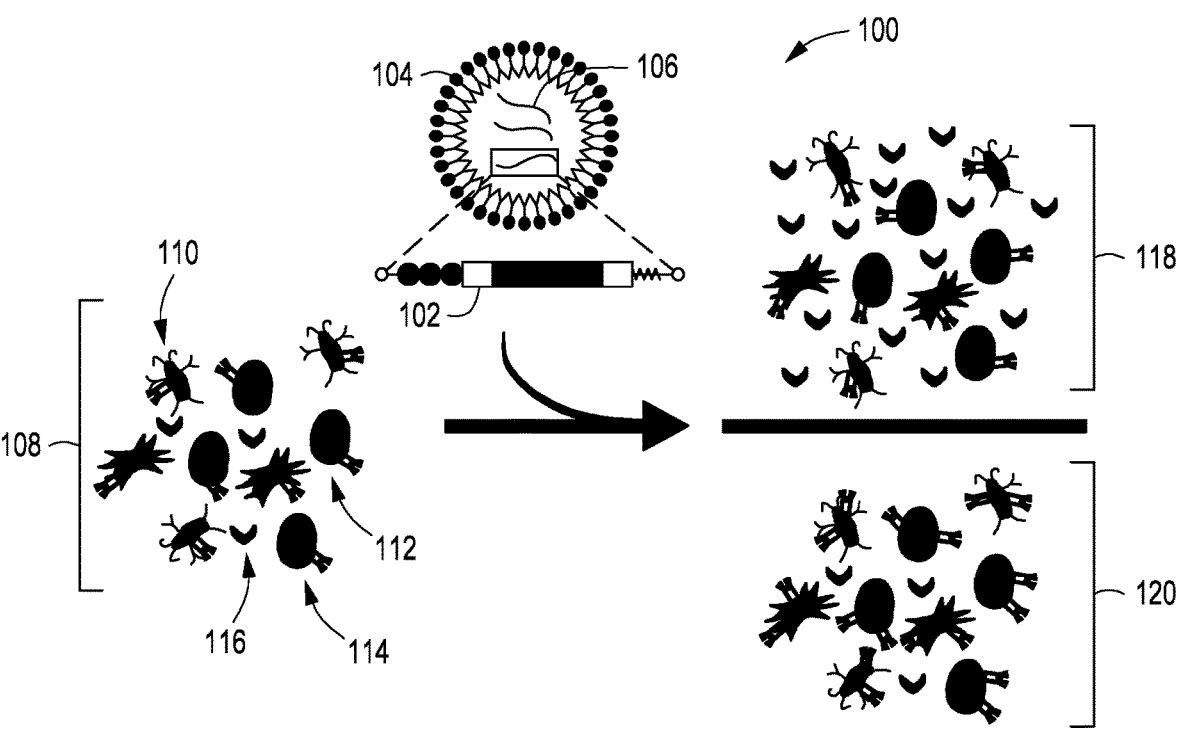
FIG. 1 is a schematic representation of mRNA transfection of a lipid carrier for overexpression of BMP and/or BMPR according to one or more aspects of the present disclosure.

The present disclosure relates to mRNA induced expression of proteins and receptors thereof and methods related thereto. More particularly, the present disclosure relates to endogenous synthetic mRNA induced overexpression of bone morphogenic protein ("BMP") and bone morphogenic protein receptor ("BMPR") within autologous bone harvest samples.

It is to be appreciated that while the present disclosure discusses the methods herein related to BMP and BMPR, the methods described herein are equally applicable to mRNA induced expression of other proteins and receptors. Such proteins and receptors may include, but are not limited to, anabolic cytokines, without departing from the scope of the present disclosure.

The present disclosure provides methodologies for mRNA induced expression of BMPs and/or BMPR(s) from collected autologous bone harvest samples and treatment methodologies related thereto. The bone harvest sample(s) is treated with lipid-solubilized mRNA encoding for one or more BMP types of interest and/or BMPR types of interest, which causes overexpression of applicable BMP(s) and BMPR(s) within the bone forming cells of the bone harvest sample(s), thereby resulting in "activated BMP material" or "aBMP." The methodologies described herein are applicable to bone formation, bone fusion, spinal fusion, and any combination thereof, without limitation.

The terms "activated BMP material" or "aBMP material," and grammatical variants thereof, as used herein, refers to bone harvest sample(s) that have been transfected with lipid-solubilized mRNA encoding for one or more BMP and/or BMPR types of interest (either or both).

The present disclosure utilizes bone harvest samples specifically as an autologous source of MSCs (mesenchymal stem cells) for endogenous mRNA induction of BMP and BMPR expression. The mRNA treated bone harvest material may be grafted (or otherwise introduced) to a bone fusion bed, where the BMP or BMPR proteins are secreted from the aBMP material and into the bone fusion bed to locally stimulate angiogenesis and activation of bone forming cells, as described in greater detail herein below.

Unlike current methodologies, treatments through mRNA induced endogenous expression of BMPs of the present disclosure advantageously provide localized treatment that reduces adverse effects (e.g., interference with non-bone biology, patient reactions, and the like, as described above) while ensuring efficacy and reduced nonunion rates. In one or more aspects, the methods of the present disclosure are believed to substantially decrease nonunion rates, such as in the range of less than about 5% nonunion, including 0% nonunion to about 5% nonunion, encompassing any value and subset therebetween. In other aspects, the methods of the present disclosure at least result in current nonunion rates of up to 30% as obtained by current rhBMP treatments without the other side effects described herein. Advantageously, the endogenous mRNA aBMP material treatments described herein, compared to current bone fusion treatments, eliminate possible contaminants, protein aggregates, or misfolded proteins present in exogenously expressed recombinant proteins. Because the treatments of the present disclosure exclusively overexpress BMP and/or BMPR in the mRNA aBMP material, the effects of BMP and/or BMPR can be targeted specifically to the fusion bed (as opposed to surrounding tissue) and the osteoinductive benefits can be realized without any or without sustained supraphysiologic dosages and associated adverse effects.

Moreover, the aBMP material treatments of the present disclosure provide a unique intraoperative methodology, thereby reducing the need for a patient to undergo a separate operation to receive BMP treatment, reducing potential complications with additional operations, reducing operational and labor costs, and the like.

Definitions

All numerical values within the detailed description and the claims herein are modified by "about" or "approximately" with respect to the indicated value, and take into account experimental error and variations that would be expected by a person having ordinary skill in the art. Unless otherwise indicated, ambient temperature (room temperature or "RT") is about 25° C.

As used in the present disclosure and claims, the singular forms "a," "an," and "the" include plural forms, unless the context clearly dictates otherwise.

The term "and/or" as used in a phrase such as "A and/or B" herein is intended to include "A and B," "A or B," "A," and "B."

For the purposes of the present disclosure and the claims thereto, the following definitions shall be used.

As used herein, the term "bone harvest sample," and grammatical variants thereof, refers to collected live bone tissue, such as live autologous bone tissue collected during a surgical procedure, whether at the surgical site or at a donor site. Bone harvest samples may include, but are not limited to, bone marrow, bone chips, bone dust, and any combination thereof.

The term "autologous," and grammatical variants thereof, as used herein, refers to tissue (or cells) obtained from the same individual. The bone harvest samples of the present disclosure that are mRNA treated to overexpress BMP and/or BMPR are collected from and used to treat the same individual, and are thus autologous bone harvest samples for use in an autologous treatment.

As used herein, the terms "bone morphogenic protein" or "BMP," and grammatical variants thereof, refer to a group of proteins that are growth factors involved in the induction of bone and cartilage formation, and belonging to the transforming growth factor beta (TGF-β) family of proteins.

As used herein, the terms "bone morphogenic protein receptor," "BMPR," or simply "receptor," and grammatical variants thereof, refer to a group of serine-threonine kinase receptors to which the TGF-β protein binds.

As used herein, the term "synthetic mRNA," and grammatical variants thereof, refers to in vitro prepared messenger ribonucleic acid (mRNA) using enzyme-mediated transcription from a linearized deoxyribonucleic acid (DNA) template. The synthetic mRNA of the present disclosure mediates BMP and/or BMPR protein translation.

As used herein, the terms "bone fusion bed" or "fusion bed," and grammatical variants thereof, refer to an area between bone or bone segments, including long bones (i.e., longer than they are wide) and vertebra, as well as other bone types (e.g., facial, skull, ribs, tarsi, metatarsi, and the like), intended by surgical intervention to be joined into a single bone structure. The aBMP material of the present disclosure is placed or otherwise introduced to such fusion beds to grow together ("fuse") bone on either side of the fusion beds.

Methods of aBMP Material Preparation and Treatment Therewith

As provided above, aBMP material is prepared and introduced to a fusion bed to secrete BMP and/or BMPR and locally stimulate angiogenesis and differentiation of pluripotent stem cells into bone forming cells, thereby inducing bone fusion.

Various bone harvest sample types may be applicable to one or more aspects of the present disclosure. Suitable bone harvest sample types include, but are not limited to, bone marrow, bone chips, bone dust, and any combination thereof. Bone marrow may be harvested from either a vertebral body or the iliac crest, such as by use of a needle and/or suction system, and may be collected intraoperatively. Bone chips or bone dust may be collected from a laminectomy (removal of the back of a vertebrae) and/or a corpectomy (removal of all or a part of a vertebral body).

In one or more aspects of the present disclosure, bone dust is utilized as the bone harvest sample, alone or in combination with one or more of the other types of bone harvest samples. Bone dust advantageously comprises, among other potential components, viable osteoblasts, osteoclasts, osteocytes, osteoprogenitor stem cells, and mesenchymal (pluripotent) stem cells (MSCs). Bone dust further advantageously demonstrates osetoinductive properties through the release of anabolic cytokines (e.g., interleukin 1 beta (IL-1β), interleukin 6 (IL-6)) and growth factors (e.g., TGF-β, vascular endothelial growth factor (VEGF), fibroblast growth factor (FGF), platelet-derived growth factor (PDGF)). These anabolic cytokines and growth factors contribute to osteoblast (bone formation cells) formation. Accordingly, the use of bone dust, a source unlike current autologous grafts, can serve as an effective source for autologous bone grafting for spinal and other bone fusions and advantageously isolates bone forming cells, allowing for specific modification before autologous fusion grafting. That is, the bone factors (BMPs and others) are not selected from another tissue source, but instead, bone itself. These factors are also present using current autologous bone grafts, as well, but are not gather intraoperatively.

Autologous bone dust may be obtained by any suitable means from a patient. It may be particularly desirable that the bone dust is collected during an intraoperative period to alleviate patient discomfort, and additionally obtain bone dust at the location of the required fusion (i.e., the surgical site). In one or more aspects of the present disclosure, the autologous bone dust for use in the methodologies and therapies of the present disclosure may be obtained using a Stryker Corporation Bone Vac (Kalamazoo, MI) collector, or other similar such collectors. The bone dust collector may be attachable to a bone drilling device to extract (e.g., suction, vacuum) bone dust concurrent with real-time surgical bone drilling.

The present disclosure provides a methodology for obtaining bone dust harvest sample(s) (e.g., using a Stryker Bone Vac or other bone dust available dust collector) and intraoperatively utilizing synthetic mRNA to induce BMP and/or BMPR expression within the bone dust harvest sample (VEGF or other osetoinductive properties, such as those mentioned above may also be induced). More particularly, the bone dust harvest sample is incubated with lipid-solubilized mRNA encoding for one or more BMP and/or BMPR types of interest, wherein the lipid is engulfed by the bone harvest sample cells and able to overexpress BMP and/or BMPR. The overexpressed proteins secrete from the bone harvest sample cells and locally stimulate angiogenesis and differentiation of MSCs or other stem cells into bone forming cells and promote activation of bone growth pathways.

It is to be noted that the advantageous components of bone dust may be additional present in full or in part in bone marrow and bone chip harvest samples, as well, and thus substituted for bone dust, depending on the particular operative procedure in which the patient is receiving, without departing from the scope of the present disclosure.

Various BMP types may be applicable to one or more aspects of the present disclosure. In one or more aspects, BMP2 and/or BMP7 may be particularly applicable, as they are both currently approved for use in bone and spinal treatment fusion therapies in various respects through the FDA. BMP2 may be particularly preferred for use in one or more aspects of the present disclosure as it exhibits potent induction of osteoblast differentiation from MSCs.

Various BMPR types may be applicable to one or more aspects of the present disclosure. Suitable BMPR types include, but are not limited to, BMPR type 1 (e.g., activin A receptor type 1 (ACVR1), bone morphogenetic protein receptor type 1A (BMPR1A), bone morphogenetic protein receptor type 1B (BMPR1B)).

Limitations to the selection of BMP and/or BMPR may include, but are not limited to, the prevalence of particular BMP and/or BMPR within the particular bone harvest sample(s), binding mechanics and translation rates, economic and availability constraints, and the like, and any combination thereof.

As provided herein, the bone harvest material of the present disclosure is treated with lipid-solubilized synthetic mRNA encoding for one or more BMP and/or BMPR types of interest. The synthetic mRNA is prepared according to standard transcription methods utilizing RNA mediated transcription from a linearized DNA template incorporating a 5' untranslated leader sequence region (UTR) and 3' polyadenylation sequence (polyA tail). One or more lipid carrier types is incubated with the synthetic mRNA (at room temperature) in traditional culture medium, such as Dulbecco's modified eagle medium (DMEM), lactated Ringer's solution, normal saline, and the like and any combination thereof and appropriate additives, to encapsulate the mRNA.

Lipid encapsulation of the mRNA may be achieved using lipids or liposomes nanoparticles (collectively referred to herein as "lipids"), lipid derivative nanoparticles, and any combination thereof. Examples of lipids may include cationic lipids, but are not limited to, tetrakis(8-methylnonyl) 3,3',3'',3'''-(((methylazanediyl) bis(propane-3,1diyl)) bis(azanetriyl))tetrapropionate; decyl(2-(dioctylammonio)ethyl) phosphate (9A1P9); ethyl 5,5-di((Z)-heptadec-8-en-1-yl)-1-

(3-(pyrrolidin-1-yl)propyl)-2,5-dihydro-1H-imidazole-2-carboxylate (A2-Iso5-2DC18); ethyl 5,5-di((Z)-heptadec-8-en-1-yl)-1-(3-(pyrrolidin-1-yl)propyl)-2,5-dihydro-1H-imidazole-2-carboxylate (A2-Iso5-2DC18); ((4-hydroxybutyl)azanediyl) bis(hexane-6,1-diyl) bis(2-hexyldecanoate) (ALC-0315); 2-[(polyethylene glycol)-2000]-N,N-ditetradecylacetamide (ALC-0159); β-sitosterol, (3S,8S,9S,10R,13R,14S,17R)-17-((2R,5R)-5-ethyl-6-methylheptan-2-yl)-10,13-dimethyl-2,3,4,7,8,9,10,11,12,13,14,15,16,17-tetradecahydro-1H-cyclopenta[a]phenanthren-3-ol; bis(2-(dodecyldisulfanyl)ethyl) 3,3'-((3-methyl-9-oxo-10-oxa-13,14-dithia-3,6-diazahexacosyl)azanediyl) dipropionate (BAME 016B); 2-(((((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)carbonyl)amino)-N,N-bis(2-hydroxyethyl)-N-methylethan-1-aminium bromide (BHEM-Cholesterol); 1,1'-((2-(4-(2-((2-(bis(2-hydroxydodecyl)amino)ethyl) (2-hydroxydodecyl)amino)ethyl) piperazin-1-yl)ethyl)azanediyl) bis(dodecan-2-ol) (C12-200); 3,6-bis(4-(bis(2-hydroxydodecyl)amino)butyl)piperazine-2,5-dione (cKK-E12); 3β-[N—(N',N'-dimethylaminoethane)-carbamoyl]cholesterol (DC-Cholesterol); (6Z,9Z,28Z,31Z)-heptatriaconta-6,9,28,31-tetraen-19-yl 4-(dimethylamino) butanoate (DLin-MC3-DMA); 1,2-dioleoyl-sn-glycero-3-phosphoethanolamine (DOPE); 2,3-dioleyloxy-N-[2-(sperminecarboxamido)ethyl]-N,N-dimethyl-1-propanaminium trifluoroacetate (DOSPA); 1,2-dioleoyl-3-trimethylammonium-propane (DOTAP); 1,2-di-O-octadecenyl-3-trimethyl-ammonium-propane (DOTMA); 1,2-distearoyl-sn-glycero-3-phosphocholine (DSPC); ethylphosphatidylcholine (ePC); hexa (octan-3-yl) 9,9',9'',9''',9'''',9'''''-((((benzene-1,3,5-tricarbonyl)yris(azanediyl)) tris (propane-3,1-diyl))tris(azanetriyl))hexanonanoate (FTT5); heptadecan-9-yl 8-((2-hydroxyethyl)(6-oxo-6-(undecyloxy)hexyl)amino) octanoate (Lipid H (SM-102)); (((3,6-dioxopiperazine-2,5-iyl)bis(butane-4,1-diyl)) bis(azanetriyl))tetrakis(ethane-2,1-diyl) (9Z,9'Z,9''Z,9'''Z,12Z,12'Z,12''Z,12'''Z)-tetrakis (octadeca-9,12-dienoate) (OF-Deg-Lin); 1,2-dimyristoyl-rac-glycero-3-methoxypolyethylene glycol-2000 (PEG2000-DMG); N1,N3,N5-tris(3-(didodecylamino) propyl)benzene-1,3,5-tricarboxamide (TT3); and any combination thereof.

The selected lipid-solubilized BMP and/or BMPR mRNA is incubated with one or more intraoperatively-obtained bone harvest samples to produce the aBMP material described herein. Incubation may take place in normal saline, 5% glucose solution, or other suitable media for perioperative storage of bone grafting materials at a temperature in the range of about 35° C. to about 39° C., encompassing any value and subset therebetween, such as about 35° C. to about 37° C. In some instances, the incubation temperature may be 37° C.±1° C., such as about 36° C., about 36.1° C., 36.2° C., 36.3° C., 36.4° C., 36.5° C., 36.6° C., 36.6° C., 36.7° C., 36.8° C., 36.9° C., or 37° C.

The aBMP material is incubated intraoperatively for at least 30 minutes to about 6 hours, such as at least 30 minutes to at least about 4 hours, encompassing any value and subset therebetween, and injected directly to or near a fusion bed, where the aBMP material overexpresses BMP and/or BMPR that is secreted from the membrane of the bone harvest sample(s) for repair and fusion at the fusion bed site. Injection may be performed using a subcutaneous port and catheter that ends at or near the fusion bed or, alternatively, the aBMP material may be transferred to a scaffold and implanted directly to the fusion bed site (e.g., when the fusion bed is exposed). A subcutaneous port and catheter may allow multiple doses to be administered over time, which may be particularly beneficial in the case of pseudarthrosis. In one or more instances, the BMP and/or BMPR mRNA or lipid-solubilized BMP and/or BMPR mRNA may be directly introduced to a fusion bed, rather than an aBMP material, without departing from the scope of the present disclosure.

Scaffold materials are biocompatible and are not considered to be particularly limiting; they may include, but are not limited to, biocompatible natural and synthetic polymers, biocompatible inorganic ceramics, biocompatible metals, and any combination thereof. For example, specific examples of suitable scaffolds may include, but are not limited to, hydroxyapatite, tricalcium phosphate, octacalcium phosphate biphasic calcium phosphate, whitlockite, bioglass, chitosan, collagen, gelatin, alginate, hyaluronic acid, polylactic acid, polyglycolic acid, polylactic-coglycolic acid, poly-ε-caprolactone, titanium mesh, stainless steel mesh, cobalt-based mesh, porous tantalum, magnesium mesh, and the like, and any combination thereof. In some instances, the scaffold may be 3D-printed, such as 3D printing of a titanium scaffold, although other materials that are biocompatible and capable of 3D-printing may also be utilized, without departing from the scope of the present disclosure.

Referring now to FIG. 1, illustrated is a schematic representation 100 of mRNA transfection of a lipid carrier for overexpression of BMP and/or BMPR according to one or more aspects of the present disclosure. mRNA 102 encoding BMP and/or BMPR is lipid-solubilized in a lipid carrier 104, where BMP and/or BMPR proteins 106 are thereby overexpressed. A bone harvest sample 108 is obtained intraoperatively, and may include bone dust, for example. The bone harvest sample 108 comprises, among other cells, osteocytes 110 and osteoblasts 112, each of which may comprise BMPRs 114 (Y-shaped). The bone harvest sample 108 may further comprise BMP 116 (crescent-shaped). The lipid-solubilized mRNA (102, 104, and 106) is incubated with the bone harvest sample 108 (right arrow). If BMP mRNA is used, overexpression of BMP occurs in aBMP material 118; if BMPR mRNA is used, overexpression of BMPR occurs in aBMP material 120. A combination of BMP mRNA and BMPR mRNA may also be used.

In one or more aspects of the present disclosure, BMPR mRNA may be modified to prevent their dephosphorylation and/or endocytosis. These modifications include, but are not limited to replacement of uridine-5'-triphosphate with N¹-methylpseudo-uridine-5'-triphosphate, poly(A) tail extension, 5' cap analogue addition, and optimization of 5' and 3'-UTR regions. These modifications enhance the translation and half-life of the mRNA and avoid immunogenicity. In doing so, and because BMP is expressed endogenously, the BMP signal of the aBMP material at a fusion site may effectively be enhanced to counteract its short half-life, as discussed hereinabove. Enhancing the BMP expression of the aBMP material applied to a fusion site may further reduce BMP concentration to further combat adverse reactions associated with high BMP concentrations. In one or more aspects of the present disclosure, the BMP mRNA and/or BMPR mRNA may be chemically altered to avoid immune response and increase stability, for example, alone or in combination with the BMPR mRNA previously described. Chemical modifications may include an extended polyA tail and/or polyuridine substitution (e.g., replacement of uridine-5'-triphosphate with N¹-methylpseudo-uridine-5'-triphosphate).

Figure 2:
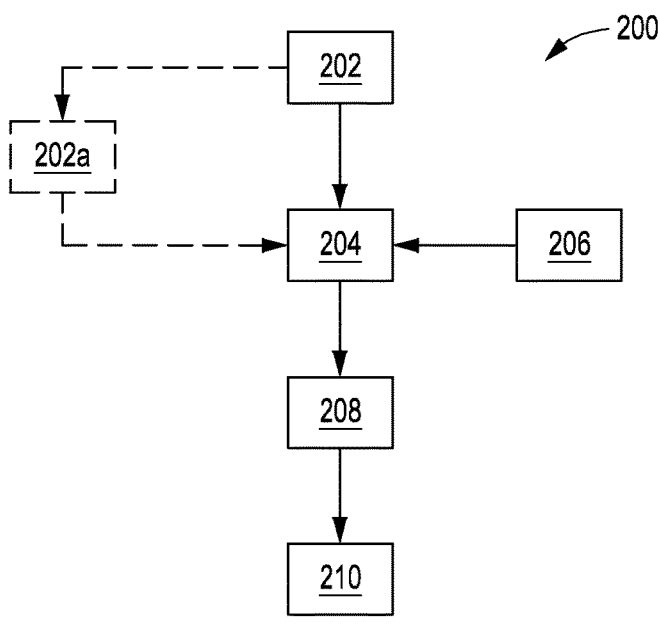
FIG. 2 is a flowchart of a method of performing an autologous intraoperative fusion procedure during an orthopedic operation, according to one or more aspects of the present disclosure.

Referring now to FIG. 2, a diagram of a method of performing an intraoperative autologous fusion procedure 200 during an orthopedic operation, according to one or more aspects of the present disclosure. The procedure includes collection of one or more bone harvest samples 202. As provided herein, the bone harvest sample 202 may include bone dust, bone chips, and/or bone marrow. Bone dust and bone chips may be collected from laminectomy or corpectomy; bone marrow may be collected from one or more of the vertebral body or iliac crest through a needle or suction system. The collected bone harvest sample(s) are combined with a lipid carrier transfected with one or more BMP mRNA and/or BMPR mRNA types 106 to produce aBMP 208 upon sterile incubation for a time of at least 30 min in a water bath at a temperature of about 37° C. (e.g., 36.9° C.). During this incubation time, the lipid encapsulating the BMP and/or BMPR mRNA is taken up by the cells of the bone harvest sample(s). In one or more aspects, prior to incubation, the cells of the bone harvest sample may be optionally separated 202a using a centrifuge, for example, to ensure that cells of interest are utilized.

With continued reference to FIG. 2, the incubated aBMP material is delivered to a fusion bed (e.g., long bone or vertebrae) 210. The aBMP may be directly introduced to the fusion bed, such as by injection using a subcutaneous port, or alternatively or in combination by utilizing a scaffold carrier, such as a collagen matrix.

Figures 3, 4A, 4B:
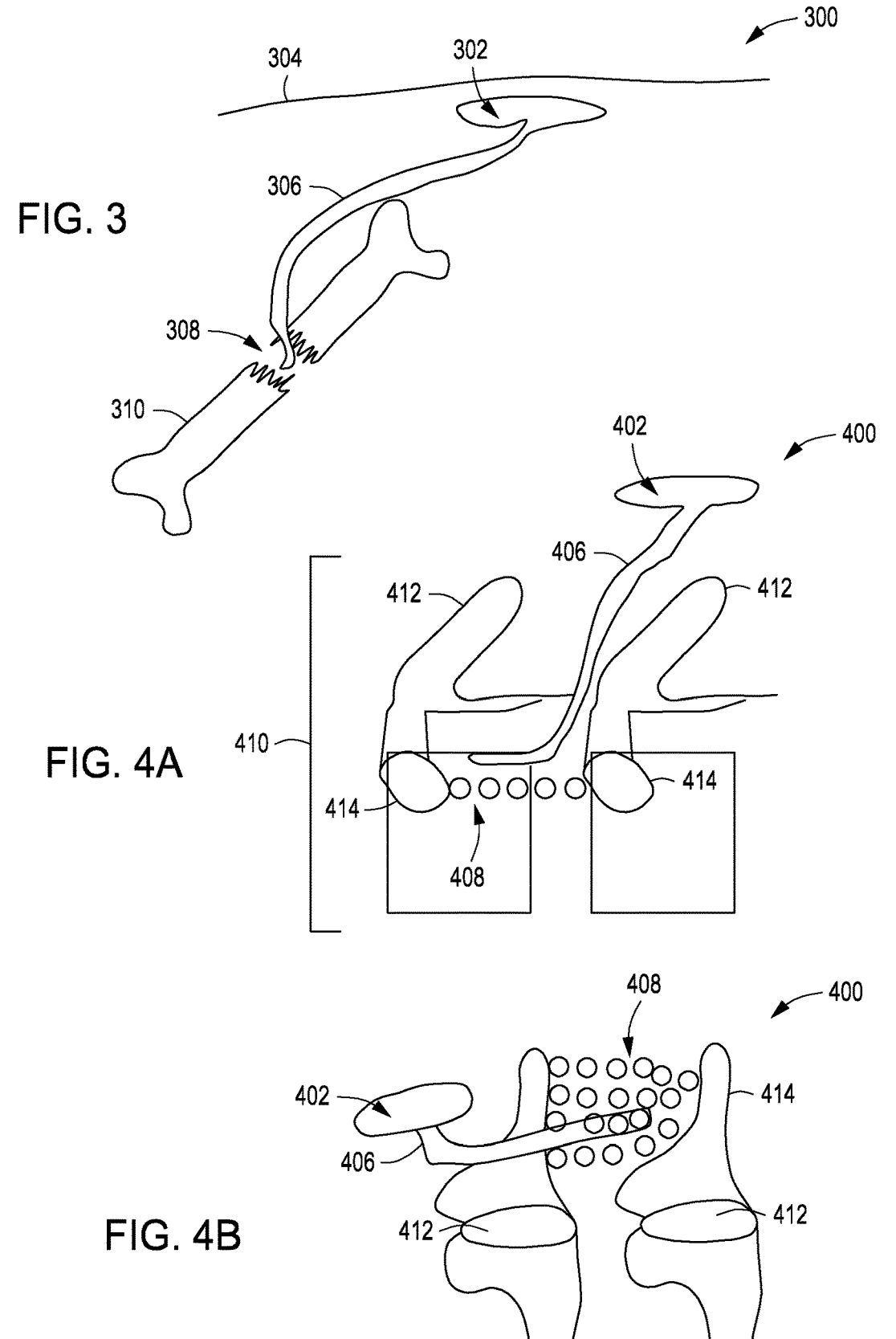
FIG. 3 is an example configuration for delivery of BMP and/or BMPR mRNA material to a fusion bed, according to one or more aspects of the present disclosure.
FIGS. 4A and 4B are example configurations for delivery of BMP and/or BMPR mRNA material to a fusion bed, according to one or more aspects of the present disclosure.

FIG. 3 shows an example configuration 300 for delivery of BMP and/or BMPR mRNA material to a fusion bed, according to one or more aspects of the present disclosure. The configuration 300 corresponds to the delivery to bed fusion bed 210 of FIG. 2. In particular, FIG. 3 illustrates the use of a subcutaneous port 302 located through the skin 304 and connected to a catheter 306 for the administration of the BMP and/or BMPR mRNA material of the present disclosure. The end of the catheter 306 is located at or near the fusion bed 308 of a long bone 310 (e.g., femur, humerus, and the like) for delivery of BMP and/or BMPR mRNA material. The long bone 310 may include a break that is either acute or the result of pseudoarsthrosis. The subcutaneous port 302 and catheter 306 will allow multiple dosing over time. Progressive fusion of the long bone 310 may be monitored over time with imaging and once adequately fused, the subcutaneous port 302 and catheter 306 may be removed through a small superficial incision in the skin 304.

The material provided to the fusion bed through the subcutaneous port 302 and catheter 306 may be BMP and/or BMPR mRNA alone in a carrier fluid, lipid-solubilized (encapsulated) BMP and/or BMPR mRNA in a carrier fluid, and/or the aBMP material in a carrier material described herein. The carrier fluid may be a lipophilic or lipophobic solution in some instances. The carrier fluid may include normal saline, lactated Ringer's, and the like, and any combination thereof. That is, the bone forming cells at the fusion site may take up or internalize (e.g., through endocytosis) the mRNA and/or lipids and overexpress BMP and/or BMPR (e.g., upon degradation of the lipid carrier); alternatively or in any combination, aBMP may be used such that a bone harvest sample(s) overexpresses BMP and/or BMPR. The optional delivery of one or more of such BMP and/or BMPR mRNA material is not limited to long bone breaks, and is equally applicable to spinal fusions and other orthopedic fractures, without limitation.

Referring now to FIGS. 4A and 4B, illustrated is a lateral view (FIG. 4A) and a superior view (FIG. 4B) of an example configuration 400 for delivery of BMP and/or BMPR mRNA material to a spinal fusion bed, according to one or more aspects of the present disclosure. The configuration 400 corresponds to the delivery to-bed fusion bed 210 of FIG. 2.

With initial reference to FIG. 4A, illustrated is the use of a subcutaneous port 402 located through the skin (see 304 of FIG. 3) and connected to a catheter 406 for the administration of the BMP and/or BMPR mRNA material (shown as a plurality of circles) of the present disclosure. The end of the catheter 406 is located at or near the fusion bed 408 between two vertebrae 410 for delivery of BMP and/or BMPR mRNA material. The vertebrae 410 each comprising a spinous process 412 and two transverse processes 414 (one shown on each vertebrae in the lateral view) may include an injury requiring vertebral fusion or be the result of pseudo-arthrosis. The subcutaneous port 402 and catheter 406 will allow multiple dosing over time. Progressive fusion of the vertebrae 410 may be monitored over time with imaging and once adequately fused, the subcutaneous port 402 and catheter 402 may be removed through a small superficial incision in the skin 304.

The material provided to the fusion bed through the subcutaneous port 402 and catheter 406 may be BMP and/or BMPR mRNA in a carrier fluid, lipid-solubilized (encapsulated) BMP and/or BMPR mRNA, and/or the aBMP material in a carrier material described herein. Carrier fluids may include, but are not limited to citrate buffered saline (particularly for the modified mRNA by itself) or lipid nanoparticles in phosphate-buffered saline, for example. That is, the bone forming cells at the fusion site may take up or internalize (e.g., through endocytosis) the mRNA and/or lipids and overexpress BMP and/or BMPR (e.g., upon degradation of the lipid carrier); alternatively or in any combination, aBMP may be used such that a bone harvest sample(s) overexpresses BMP and/or BMPR. The optional delivery of one or more of such BMP and/or BMPR mRNA material is not limited to long bone breaks, and is equally applicable to spinal fusions and other orthopedic fractures, without limitation.

FIG. 4B is a superior view of FIG. 4A, with like numerical labels for like elements.

Accordingly, the present disclosure advantageously permits treatment of bone fusion beds for long bones, spinal fusions, and other orthopedic fractures as provided herein.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

EXAMPLE EMBODIMENTS

Nonlimiting example embodiments of the present disclosure include:

Embodiment A: A method comprising: preparing a synthetic messenger ribonucleic acid (mRNA) encoding at least for a bone morphogenic protein (BMP); lipid-solubilizing the synthetic mRNA in a lipid or lipid derivative carrier, thereby forming a lipid-solubilized mRNA; obtaining intraoperatively a bone harvest sample; incubating intraoperatively the lipid-solubilized mRNA and the bone harvest sample, whereby the bone harvest sample internalizes at least a portion of the lipid-solubilized mRNA, thereby forming activated BMP material; and delivering intraoperatively the activated BMP material to a bone fusion bed.

Embodiment B: A method comprising: preparing a synthetic messenger ribonucleic acid (mRNA) encoding at least for a bone morphogenic protein receptor (BMPR); lipid-solubilizing the synthetic mRNA in a lipid or lipid derivative carrier, thereby forming a lipid-solubilized mRNA; obtaining intraoperatively a bone harvest sample; incubating intraoperatively the lipid-solubilized mRNA and the bone harvest sample, whereby the bone harvest sample internalizes at least a portion of the lipid-solubilized mRNA, thereby forming activated BMPR material; and delivering intraoperatively the activated BMPR material to a bone fusion bed.

Nonlimiting example embodiments A and B may include one or more of the following elements:

Element 1: Wherein the BMP is selected from the group consisting of BMP2, BMP7, and any combination thereof.

Element 2: Wherein the BMP is BMP2.

Element 3: Wherein the lipid or lipid derivative carrier is selected from the group consisting of tetrakis(8-methylnonyl) 3,3',3'',3'''-(((methylazanediyl) bis(propane-3,1diyl)) bis(azanetriyl))tetrapropionate; decyl(2-(dioctylammonio)ethyl)phosphate (9A1P9); ethyl 5,5-di ((Z)-heptadec-8-en-1-yl)-1-(3-(pyrrolidin-1-yl) propyl)-2,5-dihydro-1H-imidazole-2-carboxylate (A2-Iso5-2DC18); ethyl 5,5-di((Z)-heptadec-8-en-1-yl)-1-(3-(pyrrolidin-1-yl)propyl)-2,5-dihydro-1H-imidazole-2-carboxylate (A2-Iso5-2DC18); ((4-hydroxybutyl) azanediyl) bis(hexane-6,1-diyl) bis(2-hexyldecanoate) (ALC-0315); 2-[(polyethylene glycol)-2000]-N,N-ditetradecylacetamide (ALC-0159); β-sitosterol, (3S, 8S,9S,10R,13R,14S,17R)-17-((2R,5R)-5-ethyl-6-methylheptan-2-yl)-10,13-dimethyl-2,3,4,7,8,9,10,11, 12,13,14,15,16,17-tetradecahydro-1H-cyclopenta[a] phenanthren-3-ol; bis(2-(dodecyldisulfanyl)ethyl) 3,3'-((3-methyl-9-oxo-10-oxa-13,14-dithia-3,6-diazahexacosyl)azanediyl) dipropionate (BAME O16B); 2-(((((3S,8S,9S,10R,13R,14S,17R)-10,13-dimethyl-17-((R)-6-methylheptan-2-yl)-2,3,4,7,8,9,10, 11,12,13,14,15,16,17-tetradecahydro-1H-cyclopenta [a]phenanthren-3-yl)oxy)carbonyl)amino)-N,N-bis(2-hydroxyethyl)-N-methylethan-1-aminium bromide (BHEM-Cholesterol); 1,1'-((2-(4-(2-((2-(bis(2-hydroxydodecyl)amino)ethyl) (2-hydroxydodecyl) amino)ethyl) piperazin-1-yl)ethyl)azanediyl) bis(dodecan-2-ol) (C12-200); 3,6-bis(4-(bis(2-hydroxydodecyl) amino)butyl)piperazine-2,5-dione (cKK-E12); 3β-[N—(N',N'-dimethylaminoethane)-carbamoyl] cholesterol (DC-Cholesterol); (6Z,9Z,28Z,31Z)-heptatriaconta-6,9,28,31-tetraen-19-yl 4-(dimethylamino)butanoate (DLin-MC3-DMA); 1,2-dioleoyl-sn-glycero-3-phosphoethanolamine (DOPE); 2,3-dioleyloxy-N-[2-(sperminecarboxamido)ethyl]-N, N-dimethyl-1-propanaminium trifluoroacetate (DOSPA); 1,2-dioleoyl-3-trimethylammonium-propane (DOTAP); 1,2-di-O-octadecenyl-3-trimethylammonium-propane (DOTMA); 1,2-distearoyl-sn-glycero-3-phosphocholine (DSPC); ethylphosphatidylcholine (ePC); hexa(octan-3-yl) 9,9', 9'',9''',9'''',9'''''-((((benzene-1,3,5-tricarbonyl)tris (azanediyl)) tris (propane-3,1-diyl))tris(azanetriyl)) hexanonanoate (FTT5); heptadecan-9-yl 8-((2-hydroxyethyl)(6-oxo-6-(undecyloxy)hexyl)amino) octanoate (Lipid H (SM-102)); (((3,6-dioxopiperazine-2,5-iyl)bis(butane-4,1-diyl)) bis(azanetriyl))tetrakis (ethane-2,1-diyl) (9Z,9'Z,9''Z,9'''Z,12Z,12'Z,12''Z, 12'''Z)-tetrakis (octadeca-9,12-dienoate) (OF-Deg-Lin); 1,2-dimyristoyl-rac-glycero-3-methoxypolyethylene glycol-2000 (PEG2000-DMG); N1,N3,N5-tris(3-(didodecylamino) propyl)benzene-1, 3,5-tricarboxamide (TT3); and any combination thereof.

Element 4: Wherein the bone harvest sample is selected from the group consisting of bone dust, bone chips, bone marrow, and any combination thereof.

Element 5: Wherein the bone harvest sample is a combination of bone dust and bone marrow, a combination of bone dust and bone chips, or a combination of bone chips and bone marrow.

Element 6: Wherein the bone harvest sample is a combination of bone dust, bone chips, and bone marrow.

Element 7: Wherein the bone fusion bed is located in long bone, or spinal bone.

Element 8: Wherein the activated BMP material transferred into a scaffold and thereafter performing the delivery.

Element 9: wherein the activated BMP material transferred into a scaffold and thereafter performing the delivery, and wherein the scaffold is comprised of a collagen matrix.

Element 10: Wherein the delivery is performed using a subcutaneous port and a catheter, the catheter ending at or near the bone fusion bed.

Element 11: Wherein the synthetic mRNA further encodes for a bone morphogenic protein receptor.

Element 12: Wherein the synthetic mRNA further encodes for a bone morphogenic protein receptor, and wherein the BMPR is a BMPR type 1.

Embodiments A and B may be used in combination with any one, more than one, or all of Elements 1-12 without limitation.

Therefore, the present invention is well adapted to attain the ends and advantages mentioned as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
preparing a synthetic messenger ribonucleic acid (mRNA) encoding at least for a bone morphogenetic protein (BMP);
lipid-solubilizing the synthetic mRNA in a lipid or lipid derivative carrier, thereby forming a lipid-solubilized mRNA;
obtaining a bone harvest sample during a surgical procedure;
incubating the lipid-solubilized mRNA and the bone harvest sample during the surgical procedure, whereby the bone harvest sample internalizes at least a portion of the lipid-solubilized mRNA, thereby forming activated BMP material; and
delivering the activated BMP material to a bone fusion bed during the surgical procedure.

2. The method of claim 1, wherein the BMP is selected from the group consisting of BMP2, BMP7, and any combination thereof.

3. The method of claim 1, wherein the BMP is BMP2.

4. The method of claim 1, wherein the lipid or lipid derivative carrier is selected from the group consisting of tetrakis(8-methylnonyl) 3,3',3'',3'''-(((methylazanediyl) bis (propane-3,1-diyl)) bis(azanetriyl))tetrapropionate; decyl(2-(dioctylammonio)ethyl)phosphate (9A1P9); ethyl 5,5-di ((Z)-heptadec-8-en-1-yl)-1-(3-(pyrrolidin-1-yl)propyl)-2,5-dihydro-1H-imidazole-2-carboxylate (A2-Iso5-2DC18); ethyl 5,5-di((Z)-heptadec-8-en-1-yl)-1-(3-(pyrrolidin-1-yl) propyl)-2,5-dihydro-1H-imidazole-2-carboxylate (A2-Iso5-2DC18); ((4-hydroxybutyl)azanediyl) bis(hexane-6,1-diyl) bis(2-hexyldecanoate) (ALC-0315); 2-[(polyethylene glycol)-2000]-N,N-ditetradecylacetamide (ALC-0159); β-sitosterol, (3S,8S,9S,10R,13R,14S,17R)-17-((2R,5R)-5-ethyl-6-methylheptan-2-yl)-10,13-dimethyl-2,3,4,7,8,9,10,11,12, 13,14,15,16,17-tetradecahydro-1H-cyclopenta[a] phenanthren-3-ol; bis(2-(dodecyldisulfanyl)ethyl) 3,3'-((3-methyl-9-oxo-10-oxa-13,14-dithia-3,6-diazahexacosyl) azanediyl) dipropionate (BAME 016B); 2-((((((3S,8S,9S, 10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)

carbonyl)amino)-N,N-bis(2-hydroxyethyl)-N-methylethan-1-aminium bromide (BHEM-Cholesterol); 1,1'-((2-(4-(2-((2-(bis(2-hydroxydodecyl)amino)ethyl) (2-hydroxydodecyl)amino)ethyl) piperazin-1-yl)ethyl) azanediyl) bis(dodecan-2-ol) (C12-200); 3,6-bis(4-(bis(2-hydroxydodecyl)amino)butyl) piperazine-2,5-dione (cKK-E12); 3β-[N—(N',N'-dimethylaminoethane)-carbamoyl] cholesterol (DC-Cholesterol); (6Z,9Z,28Z,31Z)-heptatriaconta-6,9,28,31-tetraen-19-yl 4-(dimethylamino) butanoate (DLin-MC3-DMA); 1,2-dioleoyl-sn-glycero-3-phosphoethanolamine (DOPE); 2,3-dioleyloxy-N-[2-(sperminecarboxamido)ethyl]-N,N-dimethyl-1-propanaminium trifluoroacetate (DOSPA); 1,2-dioleoyl-3-trimethylammonium-propane (DOTAP); 1,2-di-O-octadecenyl-3-trimethyl-ammonium-propane (DOTMA); 1,2-distearoyl-sn-glycero-3-phosphocholine (DSPC); ethylphosphatidylcholine (ePC); hexa (octan-3-yl) 9,9',9'',9''',9'''',9''''''-((((benzene-1,3,5-tri-carbonyl)yris(azanediyl)) tris (propane-3,1-diyl))tris(azan-etriyl))hexanonanoate (FTT5); heptadecan-9-yl 8-((2-hy-droxyethyl)(6-oxo-6-(undecyloxy)hexyl)amino) octanoate (Lipid H (SM-102)); (((3,6-dioxopiperazine-2,5-iyl)bis(bu-tane-4,1-diyl)) bis(azanetriyl))tetrakis(ethane-2,1-diyl) (9Z, 9'Z,9''Z,9''Z,12Z,12'Z,12''Z,12''Z)-tetrakis (octadeca-9,12-dienoate) (OF-Deg-Lin); 1,2-dimyristoyl-rac-glycero-3-methoxypolyethylene glycol-2000 (PEG2000-DMG); N1,N3,N5-tris(3-(didodecylamino)propyl)benzene-1,3,5-tricarboxamide (TT3); and any combination thereof.

5. The method of claim 1, wherein the bone harvest sample is selected from the group consisting of bone dust, bone chips, bone marrow, and any combination thereof.

6. The method of claim 1, wherein the bone harvest sample is a combination of bone dust and bone marrow, a combination of bone dust and bone chips, or a combination of bone chips and bone marrow.

7. The method of claim 1, wherein the bone harvest sample is a combination of bone dust, bone chips, and bone marrow.

8. The method of claim 1, wherein the bone fusion bed is located in long bone, or spinal bone.

9. The method of claim 1, wherein the activated BMP material transferred into a scaffold and thereafter performing the delivery.

10. The method of claim 9, wherein the scaffold is comprised of a collagen matrix.

11. The method of claim 1, wherein the delivery is performed using a subcutaneous port and a catheter, the catheter ending at or near the bone fusion bed.

12. The method of claim 1, wherein the synthetic mRNA further encodes for a bone morphogenetic protein receptor.

13. A method comprising:
preparing a synthetic messenger ribonucleic acid (mRNA) encoding at least for a bone morphogenic protein receptor (BMPR);
lipid-solubilizing the synthetic mRNA in a lipid or lipid derivative carrier, thereby forming a lipid-solubilized mRNA;
obtaining a bone harvest sample;
incubating the lipid-solubilized mRNA and the bone harvest sample, whereby the bone harvest sample internalizes at least a portion of the lipid-solubilized mRNA, thereby forming activated BMPR material; and
delivering the activated BMPR material to a bone fusion bed.

14. The method of claim 13, wherein the BMPR is a BMPR type 1.

15. The method of claim 13, wherein the bone harvest sample is selected from the group consisting of bone dust, bone chips, bone marrow, and any combination thereof.

16. The method of claim 13, wherein the bone harvest sample is a combination of bone dust and bone marrow, a combination of bone dust and bone chips, or a combination of bone chips and bone marrow.

17. The method of claim 13, wherein the bone harvest sample is a combination of bone dust, bone chips, and bone marrow.

18. The method of claim 13, wherein the bone fusion bed is located in long bone, or spinal bone.

19. The method of claim 13, wherein the activated BMP material transferred into a scaffold and thereafter performing the delivery.

20. A method comprising:

obtaining a bone harvest sample during a surgical procedure;

incubating the bone harvest sample and a lipid-solubilized synthetic messenger ribonucleic acid (mRNA) encoding at least for a bone morphogenetic protein (BMP) during the surgical procedure, whereby the bone harvest sample internalizes at least a portion of the lipid-solubilized mRNA, thereby forming activated BMP material; and delivering the activated BMP material to a bone fusion bed during the surgical procedure.

\* \* \* \* \*